United States Patent
Hull, Jr. et al.

(10) Patent No.: US 8,450,383 B2
(45) Date of Patent: May 28, 2013

(54) EXTRUDED POLYMER FOAMS CONTAINING ESTERS OF A SUGAR AND A BROMINATED FATTY ACID AS A FLAME RETARDANT ADDITIVE

(75) Inventors: John W. Hull, Jr., Midland, MI (US); William J. Kruper, Jr., Sanford, MI (US); Justin C. Rowlands, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 237 days.

(21) Appl. No.: 13/125,001

(22) PCT Filed: Oct. 15, 2009

(86) PCT No.: PCT/US2009/060749
§ 371 (c)(1), (2), (4) Date: Apr. 19, 2011

(87) PCT Pub. No.: WO2010/051163
PCT Pub. Date: May 6, 2010

(65) Prior Publication Data
US 2011/0313068 A1    Dec. 22, 2011

Related U.S. Application Data

(60) Provisional application No. 61/109,953, filed on Oct. 31, 2008.

(51) Int. Cl.
*C08J 9/12* (2006.01)
*C08J 9/06* (2006.01)
*C08L 25/06* (2006.01)

(52) U.S. Cl.
USPC ........... 521/84.1; 521/79; 521/146; 524/30

(58) Field of Classification Search
USPC ................... 521/84.1, 79, 146; 524/30
See application file for complete search history.

(56) References Cited

U.S. PATENT DOCUMENTS

| | | | | |
|---|---|---|---|---|
| 3,359,220 A | * | 12/1967 | Wright | 521/56 |
| 4,459,213 A | * | 7/1984 | Uchida et al. | 252/8.05 |
| 4,705,690 A | * | 11/1987 | Brand et al. | 426/590 |
| 5,171,757 A | * | 12/1992 | Stobby et al. | 521/85 |
| 2008/0287559 A1 | | 11/2008 | King et al. | |
| 2009/0008236 A1 | | 1/2009 | Leng et al. | |
| 2009/0292079 A1 | | 11/2009 | Murray et al. | |
| 2010/0004402 A1 | | 1/2010 | King et al. | |
| 2010/0317757 A1 | | 12/2010 | King | |

FOREIGN PATENT DOCUMENTS

| | | |
|---|---|---|
| WO | 2007058736 A | 5/2007 |
| WO | 2008021417 A | 2/2008 |
| WO | 2008021418 A | 2/2008 |
| WO | 2009108453 A | 9/2009 |

* cited by examiner

*Primary Examiner* — Randy Gulakowski
*Assistant Examiner* — Kara Boyle
(74) *Attorney, Agent, or Firm* — Gary C Cohn PLLC

(57) ABSTRACT

An ester of a sugar and a brominated fatty acid is a useful FR additive for combustible polymers. The brominated FR additives unexpectedly are stable at the extrusion temperatures, and provide excellent flame retardancy to the combustible polymers.

13 Claims, No Drawings

EXTRUDED POLYMER FOAMS CONTAINING ESTERS OF A SUGAR AND A BROMINATED FATTY ACID AS A FLAME RETARDANT ADDITIVE

This application claims priority from U.S. Provisional Patent Application No. 61/109,953, filed 31 Oct. 2008.

The present invention relates to extruded polymer foams, such as expanded stryrenic polymers and copolymers, which contain flame retardant agents based on a brominated fatty acid.

Flame retardant (FR) additives are commonly added to extruded polymer foam products that are used in construction and automotive applications. The presence of the FR additive allows the foam to pass standard fire tests as are required in various jurisdictions. Various low molecular weight (<~1000 g/mol) brominated compounds are used as FR additives in these foam products. Many of these, such as hexabromocyclododecane, are under regulatory and public pressures that may lead to restrictions on their use, and so there is an incentive to find a replacement for them.

An alternative FR additive for extruded polymer foams should be capable of allowing the foam to pass standard fire tests when incorporated into the foam at reasonably low levels. Because extruded foams are processed at elevated temperatures, it is important that the FR additive be thermally stable at the temperature conditions used in the extrusion process. For some foams such as polystyrene and styrene copolymer foams, these temperatures are often 180° C. or higher. Several problems are encountered if the FR additive decomposes during the extrusion process. These include loss of FR agent and therefore loss of FR properties, and the generation of decomposition products (such as HBr) that are often corrosive and therefore potentially dangerous to humans and harmful to operating equipment. The FR agent should not cause a significant loss of desirable physical properties in the polymer. It is preferable that the FR additive has low toxicity and is not highly bioavailable.

Brominated vegetable oils have been described in U.S. Pat. No. 3,359,220 as FR additives for use in bead foam applications. As described in U.S. Pat. No. 3,359,220, the brominated vegetable oil is added into a suspension polymerization process, and is in that manner incorporated into polymer particles which are then expanded by contact with steam. The polymer particles are a polystyrene that is copolymerized with tung oil. The brominated vegetable oils are described in U.S. Pat. No. 3,359,220 as decomposing in the temperature range of 140-180° C. The bead foam process does not require high processing temperatures, as the polymerization and expansion steps are conducted at temperatures of only up to about 115° C. These steps are conducted at temperatures well below the reported decomposition temperature of the brominated vegetable oil, and so the decomposition of the brominated vegetable oils is not a problem with their use in polystyrene bead foam applications.

PCT/US2008/070171 describes certain brominated fatty acids, esters, amides or ester-amides of brominated fatty acids, glycerides of one or more brominated fatty acids and polymerized brominated fatty acids as being useful flame retardants for polystyrene foam.

The present invention is an ester of a sugar and a brominated fatty acid.

The present invention is also a blend comprising at least one combustible organic polymer and an ester of a sugar and a brominated fatty acid.

The present invention is in another aspect a method of imparting flame retardant properties to a combustible organic polymer, comprising blending the combustible organic polymer with an ester of a sugar and a brominated fatty acid.

For purposes of this invention, flame retardant properties are considered to be imparted to a combustible organic polymer if any one or more of the following criteria are seen:

(1) An increase in limiting oxygen index (LOI) of at least 0.5 units, as determined in accordance with ASTM D2863, relative to an otherwise like composition that does not contain a ester of a sugar and a brominated fatty acid;

(2) A reduction of at least once second in the time required for extinguishment, as determined according to the so-called "FP-7" test, which is described by A. R. Ingram *J. Appl. Poly. Sci.* 1964, 8, 2485-2495, relative to an otherwise like composition that does not contain an ester of a sugar and a brominated fatty acid; or (3) A "pass" rating, together with a reduction in the flame height, flame extinction time and/or formation of burning droplets as determined according to any of the DIN 4102 part 1, NF-P 92/501/4/5, SIA 183 and EN ISO 11925-2 tests, relative to an otherwise like composition that does not contain a ester of a sugar and a brominated fatty acid.

An amount of an ester of an sugar and a brominated fatty acid (sometimes referred to herein by the shorthand "sugar/brominated fatty acid ester"), which imparts flame retardant properties to a combustible organic polymer according to any of the foregoing criteria, is considered for purposes of this invention to be a "flame retarding amount".

The invention is in another aspect a process for making a foam of a combustible polymer, comprising forming a pressurized, molten mixture of (A) a combustible organic polymer, (B) a flame retarding amount of at least one ester of a sugar and a brominated fatty acid, and (C) a blowing agent, and extruding the mixture into a region of reduced pressure such that the mixture expands and cools to form an expanded polymer containing component (B).

In another aspect, the invention is an extruded blend of a combustible organic polymer and a flame retarding amount of an ester of a sugar and a brominated fatty acid.

In any of the foregoing aspects of the invention, the combustible organic polymer preferably is a polymer or copolymer of a styrenic monomer. Examples of such polymers include polystyrene homopolymers and copolymers of styrene such as styrene-acrylic acid copolymers and styrene-acrylonitrile copolymers.

The sugar/brominated fatty acid ester provides excellent FR properties to combustible polymers, as indicated by various standard tests. The sugar/brominated fatty acid esters are often effective at small levels, especially when used in conjunction with a melt flow promoter. The sugar/brominated fatty acid esters can be up to twice as effective, on the basis of the weight of bromine in the extruded polymer foam, as hexabromocyclododecane, especially when used in conjunction with a melt flow promoter. Another advantage of the invention is that the sugar/brominated fatty acid esters undergo little or no thermal degradation under the conditions at which many of the most common combustible polymers are melt processed. Therefore, the sugar/brominated fatty acid ester additive is not consumed or degraded significantly during melt processing operations such as, for example, an extrusion foaming process. Because of this, little or no loss of FR properties is seen in the extruded product, and little generation of HBr or other decomposition products occurs during the melt processing operation.

In certain embodiments, extruded polymer foam is made in the presence of the sugar/brominated fatty acid ester, using water or carbon dioxide (or both) as all of or part of the blowing agent. The sugar/brominated fatty acid esters of the invention have been found to be stable under the extrusion conditions, even in the presence of water and/or carbon dioxide, both of which are capable of engaging in hydrolysis reactions with esters and brominated aliphatic compounds. No significant loss of molecular weight by the sugar/brominated fatty acid ester is seen when water and/or carbon dioxide are present as a blowing agent in the extrusion process.

In this invention, an ester of a sugar and a brominated fatty acid is used as a flame retardant. By "sugar", it is meant a monosaccharide, disaccharide or oligosaccharide, which, prior to being esterified, contains from 5 to 16, more preferably from 5 to 12, and even more preferably from 5 to 8 hydroxyl groups per molecule. Disaccharides such as sucrose, lactose, maltose and trehalose are preferred sugars, with sucrose being especially preferred on the basis of its ready availability and low cost. Mixtures of sugars can be used if desired.

By "fatty acid", it is meant a straight-chain monocarboxylic acid that contains a chain of from 12 to 30 carbon atoms, including the carbonyl carbon of the carboxylic acid group. The fatty acid preferably contains from 12 to 24 carbon atoms, and more preferably contains from 14 to 20 carbon atoms. An "unsaturated fatty acid" in addition contains, prior to bromination, at least one site of carbon-carbon unsaturation, i.e., at least one carbon-carbon double or triple bond.

A fatty acid group is said to be "brominated" when bromine has been added across at least one site of carbon-carbon unsaturation of a fatty acid group, to introduce bromine atoms onto adjacent carbon atoms at the site of the unsaturation. The site of unsaturation is removed when the site is brominated. The brominated fatty acid groups each may contain from 2 to 8 bromine atoms.

The sugar/brominated fatty acid ester preferably contains enough brominated fatty acid groups to provide the sugar/brominated fatty acid ester with at least 25% by weight bromine. The bromine content may be any greater amount, but a practical upper limit is about 55% by weight. An especially suitable sugar/brominated fatty acid ester contains from 35 to 45% or from 35 to 40% by weight bromine. The bromine content of the sugar/brominated fatty acid ester will depend on (1) the number of brominated fatty acid ester groups per ester molecule and (2) the average number of bromine atoms per fatty acid ester group.

It is not necessary that all of the hydroxyl groups of the sugar be esterified with the brominated fatty acid. In some embodiments, one or more of the hydroxyl groups are not esterified at all. In other embodiments, one or more of the hydroxyl groups are esterified to form an ester group that is not brominated. A non-brominated ester group in such a case may be a saturated fatty acid group that contains from 12 to 30, preferably from 12 to 24 and more preferably from 14 to 20 carbon atoms.

In some embodiments, the sugar portion of the sugar/brominated fatty acid ester can contain, in addition to the brominated fatty acid ester groups, both non-esterified hydroxyl groups and hydroxyl groups which have esterified to form a non-brominated ester group.

Suitable sugar/brominated fatty acid esters can be represented by structure I:

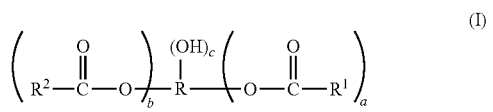

(I)

wherein R is the residue, after removal of hydroxyl groups, of a monosaccharide, disaccharide or oligosaccharide having from 5 to 16 hydroxyl groups, each $R^1$ is independently a linear $C_{11-29}$ alkyl or alkenyl group which is substituted with at least two bromine atoms and may contain additional inert substitution, each $R^2$ is independently a linear unsubstituted or inertly substituted $C_{11-29}$ alkyl or alkenyl group which does not contain bromine atoms and which may contain additional inert substitution. a is at least one, b is zero or a positive number, c is zero or a positive number and a+b+c equals the number of hydroxyl groups on the sugar. a+b+c is preferably from 5 to 12, more preferably from 5 to 8 and most preferably 8. a is preferably at least 4. When a+b+c is 8 or more, a is more preferably at least 5. b is preferably 0, 1 or 2. c is preferably zero, 1, 2 or 3 and more preferably zero, 1 or 2. b+c is preferably 4 or less and more preferably 3 or less.

In certain specific embodiments, the sugar/brominated fatty acid ester contains 5 to 16, preferably from 5 to 12, more preferably from 5 to 8, fatty acid ester groups per molecule, of which fatty acid groups at least 70%, up to 100%, by number are brominated, such that the sugar/brominated fatty acid ester contains from 35 to 45% by weight of bromine. In such embodiments, the sugar is most preferably a disaccharide such as sucrose, lactose, maltose or trehalose.

An specific type of sugar/brominated fatty acid ester that is useful herein is an ester of sucrose, lactose, maltose or trehalose with at least five moles, per mole of the sugar, of brominated constituent fatty acids of soybean oil, sunflower oil, canola oil, linseed oil, corn oil, rapeseed oil, or a combination of any two or more thereof, which sugar/brominated fatty acid ester contains from 35 to 45% by weight bromine.

An especially preferred sugar/brominated fatty acid ester is a hexa-, hepta- or octa ester of sucrose and a mixture of brominated $C_{16}$-$C_{18}$ is fatty acids, or a mixture of such esters, having a bromine content of from 35-45% by weight. Such an especially preferred sugar/brominated fatty acid ester can be represented by structure II:

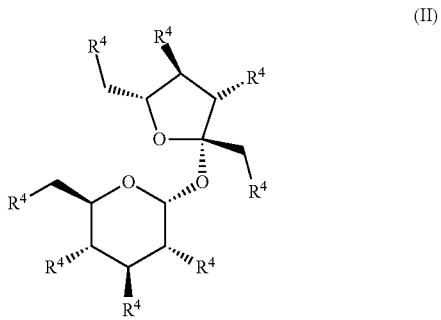

(II)

wherein at least 6 of the $R^4$ groups are linear $C_{12-30}$ carboxylic acid ester groups which are substituted with at least two bromine atoms and may contain carbon-carbon unsaturation and/or additional inert substitution. In structure II, zero, one or two of the $R^4$ groups may be hydroxyl groups and/or or linear $C_{12-30}$ carboxylic acid ester groups which may contain carbon-carbon unsaturation and/or other inert substitution but do not contain bromine groups.

The sugar/brominated fatty acid ester can be formed in a reaction of a sugar with at least one fatty acid that contains carbon-carbon double or triple bonds, or an ester of such a fatty acid, followed by brominating the resulting esterified sugar to add bromine across at least some of the carbon-carbon unsaturation sites on the fatty acid group or groups. A fatty acid ester used as a starting material is preferably a $C_1$-$C_4$ alkyl ester, and more preferably a methyl ester. Conditions for the esterification of an alcohol with a fatty acid or fatty acid ester are well known, and no unusual conditions are needed here. Typically, the reaction is performed at an elevated temperature (such as from 80 to 220° C.) so that a commercially reasonable reaction rate is obtained. A subatmospheric pressure is typically used to help remove the condensation by-products (water when a fatty acid is used as a reagent, a lower alcohol when a fatty acid ester is used) and shift the equilibrium towards the desired ester product. A catalyst such as a tin or titanium catalyst can be present to increase the reaction rate. The reaction may be performed in the presence of a solvent or diluent. At least one hydroxyl group of the sugar should be esterified to form an unsaturated fatty acid group. Any greater number of the hydroxyl groups, up to and including all of the hydroxyl groups of the sugar, may be esterified with an unsaturated fatty acid group.

The resulting ester can be brominated by reaction with elemental bromine in the general manner described in WO 2008/021418, with a quaternary ammonium tribromide in the general manner described in WO 2008/021417, or with a quaternary phosphonium tribromide. The bromination preferably should brominate at least 80%, more preferably at least 90% and even more preferably at least 98% of the carbon-carbon double or triple bonds in the fatty acid group or groups.

Alternatively, the sugar/brominated fatty acid ester can be prepared by reversing the order of the esterification and bromination reactions, i.e., by brominating an unsaturated fatty acid or an ester thereof, and then reacting the resulting brominated fatty acid or ester thereof with the sugar to form the sugar/brominated fatty acid ester. It is also possible to brominate a vegetable oil or animal fat, followed by a hydrolysis or alcoholysis step to convert the brominated oil or fat to the corresponding brominated fatty acids or fatty acid esters. The brominated fatty acids or fatty acid esters so obtained can be reacted with a sugar to form the sugar/brominated fatty acid ester.

Certain fatty acid esters of sugars are available commercially, and can be brominated to produce the sugar/brominated fatty acid ester directly. Examples of such commercially available fatty acid esters include products sold by Proctor & Gamble under the trade names Olestra™ and Sefose™.

For cost reasons, the fatty acid or fatty acid ester that is used as a starting material is preferably a fatty acid or fatty acid ester mixture obtained from a vegetable oil and/or animal fat. Vegetable oils and animal fats are triglycerides of fatty acids; the constituent fatty acids can be obtained from the starting triglycerides in known manner via hydrolysis to form fatty acids or alcoholysis with a lower alcohol, especially methanol, to form lower alkyl esters of the fatty acids, such as methyl esters of the fatty acids. The constituent fatty acids of most vegetable oils and animal fats are usually mixtures of two or more materials that may differ in chain length and/or the number of unsaturation sites. The content of a fatty acid mixture obtained in any particular case will depend on the particular plant or animal species that is the source of the oil or fat, and to a lesser extent may depend on the geographical source of the oil or fat as well as (especially in the case of vegetable oils) the time of year in which the oil or fat has been produced and other growing conditions. In many cases, at least some of the fatty acids or esters obtained from vegetable oil or animal fats will be saturated materials and therefore lack carbon-carbon double or triple bonds. Many commonly available vegetable oils, for example, have both saturated and unsaturated types among their constituent fatty acids.

Thus, a fatty acid (or fatty acid ester) mixture obtained from such a vegetable or plant often will some level of saturated materials that do not contain carbon-carbon double or triple bonds that can be brominated. When such a mixture is used to esterify the sugar, some of the resulting ester groups will lack unsaturation sites and therefore cannot be easily brominated. The presence of too many of these sites will limit the bromine content that can be achieved. Therefore, it is preferred to use a fatty acid (or fatty acid ester) mixture obtained from a vegetable oil or animal fat in which at least 70 mole percent of the constituent fatty acids contain at least one site of carbon-carbon unsaturation. Examples of suitable vegetable oils include, for example, soybean oil, safflower oil, cotton oil, linseed oil, peanut oil, olive oil, sunflower oil, canola oil, rapeseed oil, corn oil, castor oil, palm oil, hemp oil, or combinations of any two or more thereof. A starting vegetable oil may be obtained from a genetically modified organism, such as genetically modified soybean, sunflower or canola.

Sugar/brominated fatty acid esters produced using a fatty acid mixture from a vegetable oil or animal fat will necessarily be a mixture of materials. If a more highly defined sugar/brominated fatty acid ester is required, the fatty acid (or ester) mixture may be purified before using it to esterify the sugar. The purification can be more or less rigorous. In some cases, a single fatty acid (or ester) species may be isolated from the mixture for use to make the sugar/brominated fatty acid ester. In other cases, a fatty acid (or ester) mixture may be less stringently purified, to increase the concentration of one or more desired fatty acids (or esters) while decreasing the concentration of less desired fatty acids (or esters). For example, it may be desired to reduce the concentration of saturated fatty acids or esters before producing the sugar/brominated fatty acid ester.

However, in many cases, the constituent fatty acids or esters obtained from the vegetable oil or animal fat can be used directly, with little or no separation of the constituent fatty acid or ester species. This is often highly desirable from an economic standpoint. In such cases, at least 70 molepercent of the constituent fatty acids of the starting vegetable oil or animal fat should contain at least one carbon-carbon double or triple bond.

The sugar/brominated fatty acid esters usually have excellent thermal stability, as determined by a 5% weight loss temperature analysis. The 5% weight loss temperature is measured by thermogravimetric analysis as follows: ~10 milligrams of the sugar/brominated fatty acid ester are analyzed using a TA Instruments model Hi-Res TGA 2950 or equivalent device, with a 60 milliliters per minute (mL/min) flow of gaseous nitrogen and a heating rate of 10° C./min over a range of from room temperature (nominally 25° C.) to 600° C. The mass lost by the sample is monitored during the heating step, and the temperature at which the sample has lost 5% of its weight at 100° C. (after removal of volatiles from the sample) is designated the 5% weight loss temperature (5% WLT). This method provides a temperature at which a sample has undergone a cumulative weight loss of 5 wt %, based on the weight of the sample after removal of volatiles. The sugar/brominated fatty acid ester preferably exhibits a 5% WLT of at least the temperature at which the combustible polymer is melt-processed, either to blend it with the sugar/brominated fatty acid ester or to process the blend into an article such as a foam, extruded part, molded part, or the like. The 5% WLT of the sugar/brominated fatty acid ester is often in excess of 200° C., preferably in excess of 220° C. and even more preferably in excess of 240° C.

The sugar/brominated fatty acid ester is useful as a flame retardant additive for a variety of combustible polymers. "Combustible" here simply means that the polymer is capable of being burned. Combustible polymers of interest include polyolefins such as polyethylene (including copolymers of ethylene such as ethylene-alpha-olefin copolymers), polypropylene and the like; polycarbonates and blends of polycarbonates such as blends of a polycarbonate with a polyester; polyamides; polyesters; epoxy resins; polyurethanes; and vinyl aromatic polymers (including vinyl aromatic homopolymers, vinyl aromatic copolymers, or blends of one or more vinyl aromatic homopolymers and/or vinyl aromatic copolymers), as well as other flammable polymers in which the sugar/brominated fatty acid ester can be dissolved or dispersed. A "vinyl aromatic" polymer is a polymer of an aromatic compound having a polymerizable ethylenically unsaturated group bonded directly to a carbon atom of an aromatic ring. Vinyl aromatic monomers include unsubstituted materials such as styrene, divinylbenzene and vinyl naphthalene, as well as compounds that are substituted on the ethylenically unsaturated group (such as, for example alpha-methylstyrene), and/or are ring-substituted. Ring-substituted vinyl aromatic monomers include those having halogen, alkoxyl, nitro or unsubstituted or substituted alkyl groups bonded directly to a carbon atom of an aromatic ring. Examples of such ring-substituted vinyl aromatic monomers include 2- or 4-bromostyrene, 2- or 4-chlorostyrene, 2- or 4-methoxystyrene, 2- or 4-nitrostyrene, 2- or 4-methylstyrene and 2,4-dimethylstyrene. Preferred vinyl aromatic monomers are styrene, alpha-methyl styrene, 4-methyl styrene, and mixtures thereof. Expanded polymers of any of these types are of interest.

A combustible polymer of interest is a polymer or copolymer of a vinyl aromatic monomer, such as a styrene polymer, or a styrene copolymer such as a styrene-acrylic acid copolymer, a styrene-acrylonitrile (SAN) copolymer, or a styrene-acrylonitrile-butadiene (ABS) resin. Polystyrene, styrene-acrylic acid and SAN resins are especially preferred. Another combustible polymer of interest is a random, block or graft copolymer of butadiene and at least one vinyl aromatic monomer, especially styrene. Still another combustible polymer of interest is polyphenylene oxide.

Blends of a combustible polymer and the sugar/brominated fatty acid ester in accordance with the invention will contain a flame retarding amount of the sugar/brominated fatty acid ester. For purposes of this invention, flame retardant properties are indicated by the performance of the blend in limiting oxygen index (LOI) test per ASTM D2863, a time-to-extinguish test such as the so-called "FP-7" test, which is described by A. R. Ingram J. Appl. Poly. Sci. 1964, 8, 2485-2495, or other standardized tests such as DIN 4102 part 1, NF-P 92/501/4/5, SIA 183 and EN ISO 11925-2 tests, as discussed before. Generally, enough of the sugar/brominated fatty acid ester is present so as to provide the polymer composition with at least 0.1 part by weight of bromine per 100 parts of combined weight of the combustible polymer and sugar/brominated fatty acid ester. Enough can be used to provide the polymer composition with at least 0.5 part by weight bromine, with at least 0.8 part by weight bromine, or at least 1.0 part by weight bromine, on the same basis. Enough of the sugar/brominated fatty acid ester can be used to provide the polymer composition with as much as 30 parts by weight bromine, with as much as 20 parts by weight bromine, as much as 10 parts by weight bromine, as much as 5 parts by weight bromine or as much as 3 parts by weight bromine, on the same basis.

A flame retardant amount of the sugar/brominated fatty acid ester is considered to be present in a blend with a combustible polymer if the limiting oxygen index of the blend, as measured according to ASTM D2863 is increased by at least 0.5 unit, preferably by at least 1.0 unit and more preferably at least 2 units, compared to an otherwise like blend which does not contain the sugar/brominated fatty acid ester. FR performance in the LOI test may be increased by as much as 8 units or more. An extruded styrene polymer or copolymer foam containing the sugar/brominated fatty acid ester may exhibit an LOI of at least 21%, preferably at least 22% and more preferably at least 24%.

The FP-7 test, which is determined according to the method described by A. R. Ingram, J. Appl. Poly. Sci. 1964, 8, 2485-2495, measures the time required for flames to become extinguished when a polymer sample is exposed to an igniting flame under specified conditions, and the ignition source is then removed. A flame retarding amount of the sugar/brominated fatty acid ester is considered to be present in a blend if the time required for extinguishment under this test is reduced by at least one second, compared to a like blend which does not contain the sugar/brominated fatty acid ester. The time to extinguishment is preferably reduced by at least 3 seconds and even more preferably by at least 5 seconds. In absolute terms, the time to extinguishment on the FP-7 test is desirably less than 15 seconds, preferably less than 10 seconds and more preferably less than 5 seconds.

Improvement is indicated in other time-to-extinguishment or flame spread tests such as DIN 4102 part 1, NF-P 92/501/4/5, SIA 183 and EN ISO 11925-2 tests by a "pass" rating, or alternatively by a reduction in the flame height, flame extinction time and/or formation of burning droplets, as specified in the individual test methods, compared to a similar foam that does not contain the sugar/brominated fatty acid ester.

The sugar/brominated fatty acid ester is particularly useful as an FR additive for polymers which are melt-processed in the presence of the ester, especially noncellular polymers and polymer foams that are produced, in the presence of the ester, in an extrusion process. The sugar/brominated fatty acid ester exhibits surprising stability when exposed to the temperatures encountered in many melt-processing operations. Because the sugar/brominated fatty acid ester does not eliminate bromine or HBr to any significant extent at extrusion temperatures of at least 180° C., at least 190° C., at least 200° C., at least 220° C. or even 240° C. or more, the risks of injury to humans due to exposure to these decomposition products is minimized. It is especially surprising that the sugar/brominated fatty acid ester exhibits little or no hydrolysis during an extrusion process, even when water or carbon dioxide is present, as is commonly the case when those materials are used as a blowing agent. Damage to equipment is also reduced because these corrosive by-products are minimally generated, if at all, during the melt-processing operation. This allows processing equipment to be manufactured using relatively inexpensive materials of construction such as carbon steel, rather than specialized, highly corrosion-resistant steels. It is of course within the scope of the invention to incorporate a corrosion inhibitor into the molten mixture if desired to further protect against the possibility of equipment corrosion.

The sugar/brominated fatty acid ester is of particular interest as an FR additive for extruded polymer foams. In an extrusion foaming process, a molten mixture containing the combustible polymer(s), the sugar/brominated fatty acid ester, blowing agent(s) and optionally other materials is formed under sufficient pressure to keep the molten mixture from expanding. The sugar/brominated fatty acid ester can be introduced into the molten mixture by pre-blending it with the polymer(s) prior to melting the polymer(s), separately forming a concentrated "masterbatch" of the sugar/brominated fatty acid ester and a portion of the polymer(s) and mixing that masterbatch with the remainder of the polymer(s) before or after melting them, or by introducing the sugar/brominated fatty acid ester as a liquid or molten material into the melted polymer. In the process, the molten mixture containing the combustible polymer and the sugar/brominated fatty acid ester commonly is brought to a temperature of at least 180° C., often at least 190° C. or at least 200° C. before the molten mixture is extruded. Typically, this occurs at a point in the extrusion process where the combustible polymer is being mixed with other materials, such as the blowing agent. Typically (but not necessarily), the molten mixture is subsequently cooled somewhat to a suitable extrusion temperature, and is then passed through a die to a region of lower pressure, such that the mixture simultaneously cools and expands to form a cellular, expanded polymer. The expanded polymer may be open-celled, closed-celled, or contain both open and closed cells. The preferred extruded, expanded polymer contains at least 70% closed cells. The expanded polymer may be a sheet material having a thickness of not more than ¼ inch (6 mm), or may be a plank material having a thickness of from ¼ inch to 12 inches (0.6 to 30 cm), preferably from 0.5 to 8 inches (1.2 to 20 cm). The preferred extruded, expanded polymer is a styrene polymer or copolymer, most preferably polystyrene, a styrene-acrylic acid copolymer, a styrene-acrylonitrile copolymer, a styrene-butadiene copolymer or a blend of two or more thereof.

A blowing agent is used to provide a gas which generates the cells and expands the molten mixture after it passes through the die. The blowing agent may be a physical (endothermic) or chemical (exothermic) type, or a combination of both. Physical blowing agents include carbon dioxide, nitrogen, air, water, argon, C2-C8 hydrocarbons such as the various cyclic and acyclic isomers of butane or pentane, alcohols such as ethanol, and various ethers, esters, ketones, hydrofluorocarbons, chlorofluorocarbons, hydrochlorofluorocarbons and the like. Chemical blowing agents include the so-called "azo" expanding agents, certain hydrazide, semicarbazide, and nitroso compounds, sodium hydrogen carbonate, sodium carbonate, ammonium hydrogen carbonate and ammonium carbonate, as well as mixtures of one or more of these with citric acid. Another suitable type of expanding agent is encapsulated within a polymeric shell.

The amount of blowing agent that is used is sufficient to impart the desired density to the foam. The extruded polymer foam suitably has a foam density of from about 1 to about 30 pounds per cubic foot (pcf) (16-480 kg/m$^3$), especially from about 1.2 to about 10 pcf (19.2 to 160 kg/m$^3$) and most preferably from about 1.2 to about 4 pcf (19.2 to 64 kg/m$^3$).

Other materials may be present during the extrusion process and in the resulting extruded polymer foam. These include melt flow promoters, other FR agents (including hexabromocyclododecane), other halogenated FR agents and/or non-halogenated FR agents, FR synergists, IR attenuators, corrosion inhibitors, colorants, stabilizers, nucleating agents, preservatives, biocides, antioxidants, fillers, reinforcing agents and the like. These and other additives can be used if desired or necessary for the particular product or in the particular melt processing operation. It is preferred that tin compounds are substantially absent from an extrusion foaming process and the resulting extruded foam. Surprisingly, excellent FR performance and thermal stability can be obtained in the absence of these tin compounds.

Melt flow promoters are materials that, under fire conditions, help reduce the molecular weight of an organic polymer and thus allow it to melt away from the flame front or other source of heat. The melt flow promoters also are believed to assist in the liberation of HBr from the sugar/brominated fatty acid ester under conditions of high temperature, and in that manner increase the effectiveness of the sugar/brominated fatty acid ester. Examples of melt flow promoters include 2,3-dimethyl-2,3-diphenylbutane, 2,2'-dimethyl-2,2'-azobutane, bis(alpha-phenylethyl)sulfone, 1,1'-diphenylbicyclohexyl, 2,2'-dichloro-2,2'-azobutane, 2,2'-dibromo-2,2'-azobutane, 2,2'-dimethyl-2,2'-azobutane-3,3',4,4'-tetracarboxylic acid, 1,1'-diphenylbicyclopentyl, 2,5-bis(tribromophenyl)-1,3,4-thiadiazole, 2-(bromophenyl-5-tribromophenyl-1,3,4-thiadiazole and poly-1,4-diisopropylbenzene. The presence of from 0.05 to 0.5 parts by weight of a melt flow promoter per 100 parts by weight of the combustible polymer further improves FR performance at a given bromine level, or allows an equivalent improvement in FR performance to be achieved at a somewhat lower bromine content, than if the melt flow promoter is not present.

Other FR synergists can be inorganic or organic substances. Inorganic FR synergists include metal oxides (e.g., iron oxide, tin oxide, zinc oxide, aluminum trioxide, alumina, antimony trioxide and antimony pentoxide, bismuth oxide, molybdenum trioxide, and tungsten trioxide), metal hydroxides (e.g. aluminum trihydrate, magnesium hydroxide), zinc borate, antimony silicates, zinc stannate, zinc hydroxystannate, ferrocene and mixtures thereof. The organic FR synergists include halogenated paraffin, phosphorous compounds and mixtures thereof. The FR synergists may be employed in an amount from 0 to about 6 parts by weight per 100 parts by weight of the polymer.

In some embodiments of the invention, an extruded foam contains one or more IR attenuators. IR attenuators are materials that block the passage of infrared radiation through a foam, and thus reduce the transfer of heat through the foam. The effect of these materials is usually manifested as a reduced thermal conductivity, compared to an otherwise like foam in which the IR attenuator is not present. IR attenuators are often particulate solids such as aluminum oxide, titanium dioxide or, preferably, carbon black or graphite, which are dispersed throughout the polymer matrix. The particle sizes of these materials typically range from 10 nanometers to 100 microns. IR attenuators are often used in an amount of from about 0.5 to about 8 parts, preferably from 2 to 5 parts, by weight per 100 parts by weight of polymer in an extruded foam.

The use of IR attenuators in conventional foams has been related to reductions in cell size, increases in foam density and increases in the proportion of open cells. These effects are usually unwanted, particularly in making foams with larger cross-sectional areas, as they increase costs and worsen skin quality. It has been surprisingly found that these effects are reduced or even eliminated when the sugar/brominated fatty acid ester is present in the extruded foam.

The following examples are provided to illustrate the invention, but not to limit the scope thereof. All parts and percentages are by weight unless otherwise indicated.

Example 1

A commercially available, 2458 molecular weight ester of one mole of sucrose and approximately eight moles of fatty acids from a vegetable oil (Sefose 1618U oil from Proctor and Gamble, 40.4 g) is dissolved in 100 mL of methylene chloride. The ester is a mixture of species that contain about 70% by weight of the octa-ester with the rest being mainly the hexa- and hepta-esters. This ester contains 1.44 carbon/carbon double bonds per fatty acid chain, or approximately 11 carbon-carbon double bonds/molecule on average. Separately, tetraethylammonium bromide (72.1 g), 500 mL of methylene chloride and 13 mL of bromine are mixed together. The two solutions are mixed at approximately room temperature. A small amount of warming occurs when the solutions are mixed. The solution is stirred at ambient temperature for about 19 hours, during which time the solution color turns from red to orange. The mixture is then washed with 300 mL of an aqueous sodium sulfite solution. The organic phase is then washed with two 500 mL portions of purified water, and then stripped on a rotary evaporator to produce a clear orange oil. The oil is stripped further on the rotary evaporator for 5 hours at 60° C. to remove residual solvent. 73.0 grams of a viscous orange oil are obtained. The product has a molecular weight of approximately 4200 and contains 43.4% bromine by weight. The 5% WLT is 262° C.

0.92 g of the foregoing product and 49.08 g of a polystyrene homopolymer are weighed into a bottle. This mixture contains about 0.8% by weight bromine. Sufficient methylene chloride is added to the bottle to dissolve all of the contents. The solution is then cast into a large Teflon boat and allowed to dry under in a fume hood over a weekend. The resulting solids are broken up and dried in a vacuum oven at 60° C. for two hours. The resulting dried solids are compression molded into plaques, cut into small pieces and subjected to LOI and FP-7 testing. LOI is 22.5%; time to extinguishment on the FP-7 test is 1.7 seconds.

A blend made in the similar manner, but containing 1% Br also exhibits an LOI of 22.5% and a time to extinguishment of 1.7 sec on the FP-7 test.

Example 2

10 g of the Sefose 1618U material is dissolved in 100 mL of diethyl ether. The solution is cooled to between −30 and −40° C., stirred and bromine (21 g) is added dropwise over a period of 15 minutes. The mixture is allowed to warm to 15° C. and then is quenched by adding an large excess of sodium dithionate until the red color is discharged. The organic phase is washed twice with 100 mL of water, and then dried over anhydrous magnesium sulfate. The solvent is then reduced under vacuum. The product is then dissolved in n-hexane, and the solvent is evaporated to high vacuum, leaving 17 g of a very thick oil. The oil is devoid of carbon-carbon double bonds that are detectable by proton NMR. The product has a molecular weight of 4208 and contains 41.3% bromine.

What is claimed is:

1. A blend comprising at least one combustible organic polymer and an ester of a sugar and a brominated fatty acid.

2. The blend of claim 1 which contains an amount of the ester sufficient to provide the blend with from 0.5 to 30 parts by weight bromine.

3. The blend of claim 2 wherein the combustible organic polymer is a styrene homopolymer, a styrene-acrylic acid copolymer, a styrene-acrylonitrile (SAN) copolymer, a styrene-acrylonitrile-butadiene (ABS) resin, or a styrene-butadiene co- polymer.

4. A process for making a foam of a combustible polymer, comprising forming a pressurized molten mixture of (A) a combustible organic polymer, (B) a flame retarding amount of at least one ester of a sugar and a brominated fatty acid, and (C) a blowing agent, and extruding the mixture into a region of reduced pressure such that the mixture expands and cools to form an expanded polymer containing component (B).

5. The process of claim 4 wherein the foam contains a sufficient amount of the ester to provide the foam with from 0.5 to 30 parts by weight bromine.

6. The process of claim 5 wherein the combustible organic polymer is a styrene homopolymer, a styrene-acrylic acid copolymer, a styrene-acrylonitrile (SAN) copolymer, a styrene-acrylonitrile-butadiene (ABS) resin, or a styrene-butadiene copolymer.

7. An extruded combustible organic polymer comprising the blend of claim 1.

8. The blend of claim 2 wherein the ester is represented by the structure:

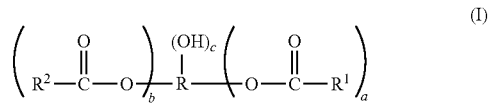

(I)

wherein R is the residue, after removal of hydroxyl groups, of a monosaccharide, disaccharide or oligosaccharide having from 5 to 16 hydroxyl groups, each $R^1$ is independently a linear $C_{11-29}$ alkyl or alkenyl group which is substituted with at least two bromine atoms and may contain additional inert substitution, each $R^2$ is independently a linear unsubstituted or inertly substituted $C_{11-29}$ alkyl or alkenyl group which does not contain bromine atoms and which may contain additional inert substitution. a is at least one, b is zero or a positive number, c is zero or a positive number, and a+b+c equals the number of hydroxyl groups on the monosaccharide, disaccharide or oligosaccharide.

9. The blend of claim 2 wherein the ester is represented by the structure:

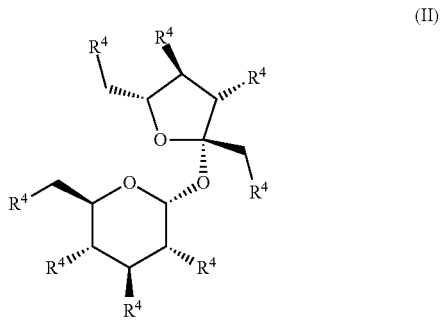

(II)

wherein at least 6 of the $R^4$ groups are linear $C_{12-30}$ carboxylic acid ester groups which are substituted with at least two bromine atoms and may contain carbon-carbon unsaturation and/or additional inert substitution, zero, one or 2 of the $R^4$ groups are hydroxyl groups and/or or linear $C_{12-30}$ carboxylic acid ester groups which may contain carbon-carbon unsaturation and/or other inert substitution but do not contain bromine groups.

10. The process of claim 5 wherein the ester is represented by the structure:

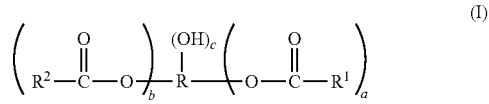

(I)

wherein R is the residue, after removal of hydroxyl groups, of a monosaccharide, disaccharide or oligosaccharide having from 5 to 16 hydroxyl groups, each $R^1$ is independently a linear $C_{11-29}$ alkyl or alkenyl group which is substituted with at least two bromine atoms and may contain additional inert substitution, each $R^2$ is independently a linear unsubstituted or inertly substituted $C_{11-29}$ alkyl or alkenyl group which does not contain bromine atoms and which may contain additional inert substitution. a is at least one, b is zero or a positive number, c is zero or a positive number, and a+b+c equals the number of hydroxyl groups on the monosaccharide, disaccharide or oligosaccharide.

11. The process of claim 5 wherein the ester is represented by the structure:

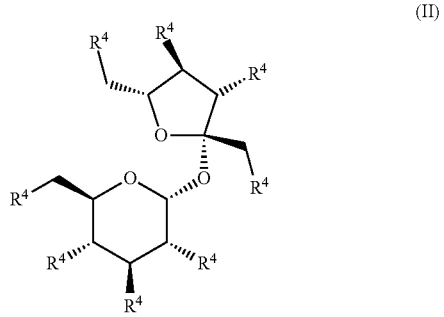

(II)

wherein at least 6 of the $R^4$ groups are linear $C_{12-30}$ carboxylic acid ester groups which are substituted with at least two bromine atoms and may contain carbon-carbon unsaturation and/or additional inert substitution, zero, one or 2 of the $R^4$ groups are hydroxyl groups and/or or linear $C_{12-30}$ carboxylic acid ester groups which may contain carbon-carbon unsaturation and/or other inert substitution but do not contain bromine groups.

12. The extruded combustible organic polymer of claim 7 wherein the ester is represented by the structure:

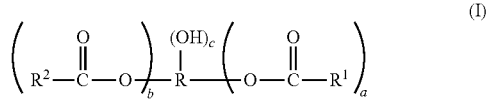

(I)

wherein R is the residue, after removal of hydroxyl groups, of a monosaccharide, disaccharide or oligosaccharide having from 5 to 16 hydroxyl groups, each $R^1$ is independently a linear $C_{11-29}$ alkyl or alkenyl group which is substituted with at least two bromine atoms and may contain additional inert substitution, each $R^2$ is independently a linear unsubstituted or inertly substituted $C_{11-29}$ alkyl or alkenyl group which does not contain bromine atoms and which may contain additional inert substitution. a is at least one, b is zero or a positive number, c is zero or a positive number, and a+b+c equals the number of hydroxyl groups on the monosaccharide, disaccharide or oligosaccharide.

13. The extruded combustible organic polymer of claim 7 wherein the ester is represented by the structure:

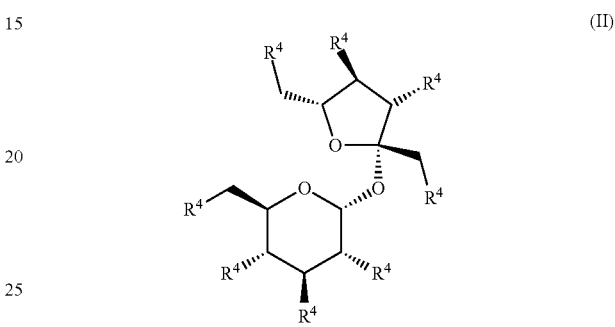

(II)

wherein at least 6 of the $R^4$ groups are linear $C_{12-30}$ carboxylic acid ester groups which are substituted with at least two bromine atoms and may contain carbon-carbon unsaturation and/or additional inert substitution, zero, one or 2 of the $R^4$ groups are hydroxyl groups and/or or linear $C_{12-30}$ carboxylic acid ester groups which may contain carbon-carbon unsaturation and/or other inert substitution but do not contain bromine groups.

* * * * *